US006541034B1

(12) United States Patent
Gergely et al.

(10) Patent No.: US 6,541,034 B1
(45) Date of Patent: Apr. 1, 2003

(54) MATRIX MATERIAL CONTAINING SUGARS AND/OR SUGAR ALCOHOLS AND PROCESS FOR ITS PREPARATION

(75) Inventors: Gerhard Gergely, Gartengasse 8, A-1053 Vienna (AT); Irmgard Gergely, Vienna (AT); Thomas Gergely, Vienna (AT)

(73) Assignee: Gerhard Gergely, Vienna (AT)

( * ) Notice: Subject to any disclaimer, the term of this patent is extended or adjusted under 35 U.S.C. 154(b) by 0 days.

(21) Appl. No.: 09/450,777

(22) Filed: Nov. 30, 1999

(30) Foreign Application Priority Data

Dec. 22, 1998 (AT) ............................................. 2130/98

(51) Int. Cl.$^7$ ............................. A61K 9/14; A61K 9/16; B01J 13/02
(52) U.S. Cl. .................... 424/490; 424/489; 427/213.33
(58) Field of Search .................. 424/484, 488, 424/489, 490; 427/213.33

(56) References Cited

U.S. PATENT DOCUMENTS

| | | | |
|---|---|---|---|
| 3,106,512 A | | 10/1963 | Williams |
| 3,658,554 A | * | 4/1972 | Hirota ........................ 99/102 |
| 4,000,326 A | | 12/1976 | Okada et al. ................ 426/126 |
| 4,692,339 A | | 9/1987 | Stetson et al. ................. 426/72 |
| 5,223,282 A | * | 6/1993 | Patel et al. ...................... 426/3 |
| 5,415,870 A | * | 5/1995 | Gergely et al. ............. 424/466 |
| 5,965,162 A | * | 10/1999 | Fuisz et al. ................. 424/464 |
| 5,972,395 A | * | 10/1999 | Saleeb et al. ................. 426/96 |

FOREIGN PATENT DOCUMENTS

| | | | |
|---|---|---|---|
| AT | | 359978 | 5/1980 |
| DE | | 25 14 982 | 8/1975 |
| DE | | 33 31 517 A1 | 3/1984 |
| EP | | 0 079 142 A1 | 5/1983 |
| EP | | 0 158 460 A1 | 10/1985 |
| EP | | 0 198 431 A2 | 10/1986 |
| EP | | 0 237 403 A1 | 9/1987 |
| EP | | 0 369 445 A2 | 5/1990 |
| EP | | 0 452 145 A2 | 10/1991 |
| GB | | 902369 | * 8/1962 |
| JP | | 49034821 B | 9/1974 |
| JP | | 63196516 A | 8/1988 |
| RU | | 1 292 700 A | 2/1987 |
| WO | | 94/06308 | * 3/1994 |
| WO | | 94/23593 | * 10/1994 |

* cited by examiner

Primary Examiner—Thurman K. Page
Assistant Examiner—S. Tran
(74) Attorney, Agent, or Firm—Oliff & Berridge, PLC

(57) ABSTRACT

A matrix material containing sugars and/or sugar alcohols serves to encapsulate solid or liquid substances, in particular pharmaceutically active substances and/or at least one pharmaceutically admitted flavor and the like. The material contains a substance that during cooling from its melt largely suppresses crystallization of the melt. The substance can be, for example, an inner ester of a hydroxy acid, particularly gluconic acid delta-lactone. The suppression of crystallization can be achieved by adding a small amount of a pharmaceutically admitted, and preferably weak, acid, such as lactic acid or malic acid, that simultaneously reduces the risk of saponification by alkaline components of an effervescent system that might be present.

11 Claims, No Drawings

MATRIX MATERIAL CONTAINING SUGARS AND/OR SUGAR ALCOHOLS AND PROCESS FOR ITS PREPARATION

The invention concerns a matrix material according to the preamble of claim 1 and a process for its preparation. A process for the preparation of a solid dispersion of solids such as pharmaceutical substances or taste vectors in the form of powders, or of liquid substances such as flavors, pharmaceutical substances as well as liquid concentrates or extracts in sugar has for instance been described in the Austrian patent document AT-PS-359978. Here the substances to be encapsulated are added to a mixture of several sugars under inert gas, which yields a dispersion of the substance to be protected in the sugar medium that subsequently is brought in contact with a chilled medium.

In practical applications it has now been found, however, that depending on the ratios of, for instance, mannitol, sorbitol, and glucose, or of the sugars cited in the above AT-PS, such as erythritol, mannitol, sorbitol, fructose or glucose, either a crystallization of the sugar matrix does as yet come about or the product becomes too elastic for further processing, and particularly for the required grinding, when higher quantities of fructose or glucose are employed, so that the mass gums up in the mill. Moreover, when fructose or glucose are used, discolorations can also occur, particularly when these are used in combination with alkalies, as for instance in combination with an effervescent base material when the matrix components come in contact with the alkaline effervescent components such as sodium bicarbonate or sodium carbonate.

It was the task set for the invention, therefore, on one hand to eliminate the disadvantages mentioned above and find an improved composition for a suspension of liquid components such as flavors, and also to better encapsulate solid components and optimize the process. Surprisingly, this has been successfully achieved for the first time by the characteristics cited in the specification of claim 1. Even small amounts of a weak acid can produce the desired effect. It is preferred, however, to employ gluconic acid delta-lactone. Advantageous further developments of the invention are described in the specifications of the dependent claims.

It was an additional aim to better protect the sensitive substances, on one hand against oxidation and on the other hand against saponification, which is of particular importance for flavors. Surprisingly, the use of gluconic acid delta-lactone or similar esters in a joint melt with the sugar alcohols has proven its worth, not only in preventing a possible crystallization but also in impeding the influence of oxidation and of the conditions for a saponification of sensitive active substances or liquid taste vectors. On one hand these are adapted to prevent the crystallization of mannitol or mannitol-sorbitol mixtures to a particularly high degree; on the other hand they give off minor quantities of gluconic acid when the temperature is slightly raised, so that the product is maintained at weakly acidic pH values. This therefore counteracts a saponification of sensitive substances when these are in contact with alkalies, and thus promotes stability. In addition an antioxidant such as tocopherol acetate (Vitamin E acetate) can be added to the matrix material in order to incorporate into the matrix additional protection for the active substances or flavors that are sensitive against air oxygen. Relatively small amounts will suffice for this purpose, such as 0.01 to 0.005%.

Contrary to a melt in which glucose or fructose are used together with mannitol and sorbitol, the melt according to the invention does not become as elastic and can subsequently readily be ground without gumming up the mill. This has positive aspects also for the production process, since the melt upon discharge need not be brought in contact with a medium so strongly chilled in order to solidify. It is thus no longer required that the temperature of the chilled metal surface have a maximum value of 10° C. and preferably of 0° C. Rather, slight cooling with water to 12–18° C. secures a satisfactory solidification of the melt within a corresponding period of time, so that the droplets suspended in the melt will uniformly solidify within the melt and no separation will occur. Aerosil® in an amount of 0.2 to 1% can also be added to the melt in order to attain better processability during subsequent grinding.

In a melt with sorbitol and mannitol, relatively high ratios of gluconic acid delta-lactone can be employed, such as 15 or even up to 35 wt. % referred to the finished melt. A mixture of mannitol, sorbitol, and gluconic acid delta-lactone has been found to be particularly advantageous for the desired properties, with a relatively small amount of sorbitol of about 1 to 10% for 100 parts by weight of the melt, while mannitol can be employed in amounts of 50–80%.

The matrix material may also contain a small amount of a pharmaceutically admitted—and preferably weak—acid, such as lactic acid or malic acid, which can further check the risk of saponification by the alkaline components of an effervescent system that might be present.

When using gluconic acid delta-lactone in the processing one must take into account, however, that this may already decompose to gluconic acid while being brought to melt at higher temperatures. This is prevented by first melting mannitol and sorbitol at 190° C., and adding the gluconic acid delta-lactone only during cooling of this melt, while the heat of melting required to melt the gluconic acid delta-lactone is withdrawn from the molten mannitol-sorbitol mixture. One thus arrives at a precisely predetermined cooling to 150° C.

As already mentioned, one can add to the melt Aerosil® in an amount of 0.2 to 0.8 wt. % prior to pouring the melt, in order to prevent a later gumming up in the mill.

This mass becomes highly viscous already at 135° C., so that liquid substances are introduced with the aid of high shear forces in a temperature range of preferably 150 and 146° C. A special arrangement is used to keep the mixture at this temperature. Subsequently the mixture is poured onto a turning conveyor belt made of teflonized textile and having a total length of about 20 to 40 m. The upper part of the belt is supported by a water-cooled metal surface at 12–15° C. After 10 to 20 m the product has sufficiently solidified so that it can then be comminuted by an impact device and fed to subsequent grinding.

The dry flavors thus produced have the advantage of remaining stable for many years, since the oil droplets enclosed within the particles are completely closed off from the air and hence are protected against oxidation or other external effects. Moreover, small amounts of gluconic acid are formed, as already mentioned as well, during the gentle melting of gluconic acid delta-lactone, so that an optimum pH situation is also present in the solid noncrystalline melt, and the matrix is readily maintained at slightly acidic pH. This provides additional protection against saponification.

When this process is used, an inert gas atmosphere need not be created, since the operations are extremely rapid and unbroken.

Below some examples are provided:

EXAMPLE NO. 1
(Use of the Melt for Liquid Flavors)

In a melting pot, 68 parts by weight of mannitol and 2 parts by weight of sorbitol are melted. At 190° C., 30 parts by weight of gluconic acid delta-lactone are introduced and brought to melt under continuous stirring, while because of the heat needed for the melting of the gluconic acid delta-lactone a temperature of 148–150° C. is attained. At 150° C., seven parts by weight of the liquid flavor substance are then stirred in under pressure, subsequently the melt is poured out onto a belt cooled to a temperature of about 12–15° C. where it will solidify within 20 minutes, so that a separation of the oils in the melt cannot occur. After some time the melt can be broken into pieces and then ground.

EXAMPLE NO. 2
(Introduction of Solid Substances into the Melt)

The introduction of a solid substance, for instance a heat-stable active substance, into the melt can occur in the same manner, in which case after the melting of the gluconic acid delta-lactone—for instance in an amount of up to 20 parts by weight—finely micronized active substance is introduced into the melt and dispersed with a high-pressure stirrer. The melt is subsequently poured out and cooled down on a belt.

EXAMPLE NO. 3

As a base for encapsulation, the melt can also have the following composition: 10 parts by weight of sorbitol are melted with 70 parts by weight of mannitol at 190° C.; as described above, 20 parts by weight of gluconic acid delta-lactone are then added. Liquid or solid components can be introduced into the resulting melt, distributed with a turbine stirrer, the melt can then be poured out and made to solidify. The melt can subsequently be ground and sifted to the desired grain size.

What is claimed is:

1. Matrix material for the encapsulation of solid or liquid substances comprising a solidified melt of sugars and/or sugar alcohols, wherein said matrix material further contains a substance selected from the group consisting of an inner ester of a hydroxy acid present in an amount of 10 to 50 wt. % relative to the total amount of matrix material and a pharmaceutically admitted acid present in an amount of 0.1 to 10 wt. % of the matrix material.

2. The matrix material according to claim 1, wherein said inner ester of a hydroxy acid is gluconic acid delta-lactone.

3. The matrix material according to claim 1, wherein the solid or liquid substances are selected from the group consisting of pharmaceutically admitted active substances and flavors.

4. The matrix material according to claim 1, wherein the matrix material further comprises a pharmaceutically admissible antioxidant.

5. The matrix material according to claim 4, wherein the antioxidant is Vitamin E.

6. The matrix material according to claim 1, wherein the sugar alcohols are mannitol and sorbitol.

7. The matrix material according to claim 6, comprising 1 to 10% of sorbitol for 100 parts by weight of the melt and 50 to 80% of mannitol for 100 parts by weight of the melt.

8. The matrix material according to claim 1, wherein the pharmaceutically admitted acid is lactic acid or malic acid.

9. A process for the preparation of a matrix material according to claim 1, comprising melting at least one substance from the group of sugars and/or sugar alcohols is heating to a temperature which is higher than their melting point, then introducing into the melt under mixing at least one component suppressing crystallization selected from the group consisting of an inner ester of a hydroxy acid and a pharmaceutically admitted acid, the said temperature being also higher than the highest melting point of the component suppressing the crystallization, and finally introducing, again under mixing, at least one solid and/or liquid substance, whereupon the mixture is cooled down.

10. The process according to claim 9, wherein at least one solid and/or liquid substance is selected from the group consisting of pharmaceutically admissible active substances and flavors.

11. The process according to claim 9, wherein the process further comprises comminuting the final mixture.

* * * * *